US007422869B2

(12) United States Patent
Eda et al.

(10) Patent No.: US 7,422,869 B2
(45) Date of Patent: *Sep. 9, 2008

(54) METHOD FOR DIAGNOSING INFECTIOUS DISEASES

(75) Inventors: Shigetoshi Eda, Knoxville, TN (US); Clarence A. Speer, Louisville, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 11/701,202

(22) Filed: Feb. 1, 2007

(65) Prior Publication Data

US 2007/0141653 A1    Jun. 21, 2007

Related U.S. Application Data

(63) Continuation of application No. 10/832,761, filed on Apr. 27, 2004, now Pat. No. 7,276,350.

(51) Int. Cl.
*C12Q 1/02* (2006.01)
*G01N 33/53* (2006.01)
*A61K 39/04* (2006.01)
*A61K 39/02* (2006.01)
*A61K 39/38* (2006.01)

(52) U.S. Cl. .................... 435/29; 424/9.1; 424/9.2; 424/130.1; 424/164.1; 424/184.1; 424/234.1; 424/248.1; 435/4; 435/7.1; 435/7.2; 435/40.5; 436/501; 436/536

(58) Field of Classification Search ................ 424/9.1, 424/9.2, 130.1, 164.1, 184.1, 234.1, 248.1; 435/4, 7.1, 7.2, 29, 40.5; 436/501, 536

See application file for complete search history.

(56) References Cited

OTHER PUBLICATIONS

Harris, BN and Barletta, RG, "*Mycobacterium avium* subsp. *paratuberculosis* In Veterinary Medicine", Clinical Microbiology Reviews, 14(3):489-512 (2001).

Linnabary, RD, et al, "Johne's Disease in Cattle", Council for Agricultural Science and Technology, 17:1-10 (2001).

Kennedy, DJ, and Benedictus, G, "Control of *Mycobacterium avium* susp. *paratuberulosis* Infection in agricultural species", Rev Sci Tech, 20:151-179 (2001).

Whitlock, RH, et al, ELISA and fecal culture for paratuberculosis (Johne's disease): sensitivity and specificity of each method, Veterinary Microbiology, 77:387-398 (2000).

Fang, Y, et al, Comparison of Real-Time, Quantitative PCR with Molecular Beacons to Nested PCR and Culture Methods for Detection of *Mycobacterium avium* subsp. *paratuberulosis* in Bovine Fecal Samples, J. Clin. Microbiology, 40(1):287-291 (2002).

Motiwala, AS, et al, "Molecular Epidemiology of *Mycobacterium avium* subsp. *paratuberulosis*: Evidence for Limited Strain Diversity, Strain Sharing, and Identification of Unique Targets for Diagnosis", J. Clin. Microbiology, 41(5):2015-2026 (May 2003).

Collins, DM, et al, "Comparison of polymerase chain reaction tests and faecal culture for detecting *Mycobacterium paratuberulosis* in bovine faeces", Veterinary Microbiology, 36:289-299 (1993).

Vary, PH, et al, "Use of Highly Specific DNA Probes and the Polymerase Chain Reaction to Detect *Mycobacterium paratuberulosis* in Johne's Disease", J. Clin. Microbiology, 28(5):933-937 (1990).

Pillai, SR, and Jayarao, BM, "Application of IS900 PCR for Detection of *Mycobacterium avium* subsp. *paratuberulosis* Directly from Raw Milk", J. Dairy Sci., 86:1052-1057 (2002).

Ozbek, A, et al, "Evaluation of two recovery methods for detection of *Mycobacterium avium* subsp. *paratuberulosis* by PCR: direct-dilution-centrifugation and C18-carboxypropylbetaine processing", FEMS Microbiology Letters, 229:145-151(Nov. 19, 2003).

Sweeney, RW, et al, "*Mycobacterium paratuberulosis* isolated from fetuses of infected cows not manifesting signs of the disease", Am. J. Vet. Res., 53(4):477-480 (1992).

Wilks, CR, et al, "Isolation of mycobacteria inducing cross-reactions in the complement fixation test for Johne's Disease", Research in Veterinary Science, 30:323-327 (1981).

Klausen, J, et al, "Evaluation of serum and milk ELISAs for paratuberculosis in Danish dairy cattle", Preventive Veterinary Medicine, 58:171-178 (2003).

Adaska, JM, and Anderson, RJ, "Seroprevalence of Johne's-disease infection in dairy cattle in California, USA", Preventive Veterinary Medicine, 60:255-261 (2003).

Chamberlin, et al, "Review Article; *Mycobacterium avium* subsp. *paratuberulosis* as one cause of Crohn's disease", Aliment Pharmacol Ther, 15:337-346 (2001).

El-Zaatari, Fak, et al, "Etiology of Crohn's disease: the role of *Mycobacterium avium* subsp. *paratuberulosis*", Trends in Molecular Medicine, 7(6):247-252 (2001).

Meylan, M, et al, "Survival of *Mycobacterium paratuberulosis* and preservation of Immunoglobulin G in bovine colostrum under experimental conditions simulating pasteurization", Am. J. Vet. Research, 57(11);1580-1585 (1996).

Bull, TJ, et al, "Detection and verification of *Mycobacterium avium* subsp. *paratuberulosis* in fresh lieocolonic mucosal biopsy specimens from individuals with and without Crohn's Disease", J. Clinical Microbiology, 41(7):2915-2923 (Jul. 2003).

Naser, SA, et al, "Specific seroreactivity of Crohn's disease patients against p35 and p36 antigens of *Mycobacterium avium* subsp. *paratuberulosis*", Veterinary Microbiology, 77:497-504 (2000).

Cohavy, O, et al, "Identification of a novel mycobacterial histone H1 homology (HupB) as an antigenic target of pANCA monoclonal antibody and serum immunoglobulin A from patients with Crohn's Disease", Infection and Immunity, 67(12):6510-6517 (1999).

Zeus Scientific, "FTA-ABS Double Stain IFA Test", Brochure on web page www.zeussci.com/docs/r2190 (1997).

Zeus Scientific, "Toxoplasma IFA Test System", Brochure on web page www.zeussci.com/docs/r2360 (1998).

(Continued)

*Primary Examiner*—Rodney P. Swartz
(74) *Attorney, Agent, or Firm*—Howard Eisenberg, Esq.

(57) ABSTRACT

A method for diagnosing the presence in an animal of an infection due to a microorganism in which a test sample obtained from the animal is exposed to a population of the microorganism and the presence of binding of the microorganism by an antibody in the test sample is determined.

19 Claims, 2 Drawing Sheets

OTHER PUBLICATIONS

Zeus Scientific, "FTA-ABS IFA Test System", Brochure on web page www.zeussci.com/docs/r2180 (1997).

Zeus Scientific, "Mycoplasma Pneumoniae Antibody (MP) IgG Test", Brochure on web page www.zeussci.com/docs/r2270 (1997).

Zeus Scientific, "Legionella DFA Test System", Brochure on web page www.zeussci.com/docs/r2075 (1998).

Lind, A, et al, "Immunologically based diagnostic tests: Humoral Antibody Methods", in The Mycobacteria, eds, Kubica and Wayne, Marcel Dekker, Inc., New York, 1985 (pp. 221-248).

Sjursen, H. et al, "Flow cytometric assay for the measurement of serum opsonins to *Neisseria menjngitidis* serogroup B, serotype 15", J. Immunolog. methods, 116:235-243 (1989).

Tertti, R., et al, "Serum opsonic capacity against Yersinia enterocolitica O:3 in yersiniosis patients with or without reactive . . . ", Clin. Exp. Immunol., 76:227-232 (1989).

Darwin, PE et al, "Immune evasion by *Helicobacter pylori*: gastric spiral bacteria lack surface immunoglobulin deposition and reactivity . . . ", *Helicobacter*, 1(1):20-27 (1996).

Coombs, RRA, et al, "The class of antibodies sensitizing bacteria measured by mixed reverse passive antiglobulin haernagglutination (MrPAH)", Immunology, 34:1037-1044 (1978).

Groves, FD, et al, "Serum Antibodies to *Helicobacter pylori* and the CagA antigen do not explain . . . ", Cancer Epidemiology,Biomarkers & Prevention, 11:1091-1094 (2002).

Moore, JC, et al, "Age-dependent presence of antibodies in rat dams, capable of conferring protection against group B . . . ", FEMS Microbiology Letters, 202:125-127 (2001).

Jarlov, JO, et al, "Antibody response to whole cells and teichoic acid of *Staphylococcus aureus* strain E 1360 . . . ", Acta Path. Microbiol. Immunol. Scand., 95:115-120 (1987).

Gerber, MA, et al, "Recombinant outer surface protein C ELISA for the diagnosis of early Lyme Disease", J. Infectious Diseases, 171:724-727 (1995).

METHOD FOR DIAGNOSING INFECTIOUS DISEASES

This application is a continuation of U.S. patent application Ser. No. 10/832,761, now U.S. Pat. No. 7,276,350, filed Apr. 27, 2004.

FIELD OF THE INVENTION

The invention pertains to the field of diagnosing infection due to a microbial organism.

BACKGROUND OF THE INVENTION

Perhaps the most important aspect in diagnosing the cause of symptoms experienced by a patient when an infectious agent is suspected as being the cause of the symptoms is the establishment of the identity of the specific organism that is etiologically responsible for the symptoms.

Classically, the identity of an infectious microorganism has been established by isolating the organism from the body of a patient, culturing the organism on a suitable culture medium, and identifying the cultured organism based on biochemical, immunological, or other tests. This method suffers from several disadvantages. Diagnosis by culture and identification often requires a substantial period of time when growing organisms that have a slow growth rate. For example, standard culture and identification methods for *Mycobacterium avium* subsp. *paratuberculosis* may require 8 to 16 weeks or more to perform due to the very slow growth rate of this organism. Another disadvantage to culture and identification methods of diagnosis is that the particular organism causing disease in a patient may fail to grow on standard culture media, leading to a negative culture result and a failure in diagnosis. Additionally, because such methods require the isolation of an infectious organism from a patient, these methods are inappropriate at times when the patient is not shedding the organism or if the organism is located in an inaccessible location within the body of the patient.

In recent years, molecular biological and immunological methods have been developed for the diagnosis of infectious diseases. These methods generally fall into three categories, detection of genome nucleic acids, detection of protein, and detection of antibodies directed against a pathogen.

Diagnosis by identification of genome nucleic acids is typically performed using either or both amplification of DNA by polymerase chain reaction (PCR) followed by identification of PCR fragments produced or by use of probes that bind specifically to a portion of the genome of a suspected causative organism. These methods, especially when used in combination, can be very sensitive and specific methods to establish a diagnosis of a causative organism. There are several disadvantages associated with these methods. They are expensive, require sophisticated technical expertise to perform, and generally take several days to obtain enough microorganisms for a diagnosis. Another significant disadvantage associated with diagnosis by detection of genome nucleic acids is that an organism must be isolated in order to obtain the genome nucleic acids. Additionally, diagnosis based on DNA sequence may fail to distinguish between closely related microbial pathogens, such as between different strains of *Mycobacterium*, such as *Mycobacterium avium* subsp. *paratuberculosis* and *Mycobacterium avium* subsp. *avium*.

Diagnosis by identification of proteins is typically performed by an enzyme-linked immunosorbent assay (ELISA). In this test, an antigen from a test sample, typically a disrupted microorganism or a portion of a microorganism, is captured by a first antibody that is specific for the antigen of interest and which is bound to a solid support. A labeled second antibody that binds to antibodies in test serum is then exposed to the solid support complex to provide a means for identification of the presence of the antigen. ELISA tests, however, suffer from several disadvantages including low sensitivity and the requirement to provide two different antibodies for the detection of an antigen. ELISA testing requires skilled laboratory technicians and can provide false results if samples are contaminated.

An example of an infectious disease for which currently available diagnostic methods are inadequate is Johne's Disease, a disease in cattle caused by *Mycobacterium avium* subsp. *paratuberculosis* (MAP). Johne's Disease results in decreased milk production and early culling of infected cows resulting in an annual loss of approximately $1.5 billion to the agricultural industry in the United States. Considerable evidence exists that MAP is also the causative organism of Crohn's Disease in humans. Despite this significant impact on the U.S. economy and on human health, there is no effective diagnostic test to determine infection by MAP.

At present, fecal culture is considered to be the most accurate means of diagnosing Johne's Disease. However, this diagnostic test has low sensitivity (less than 50%) and is capable of detecting infections only in animals that are actively shedding MAP in their feces. Additionally, diagnosis of MAP by culture typically requires 8 to 16 weeks for growth of the organism.

Other diagnostic tests for Johne's Disease include PCR, complement fixation, agar gel immunodiffusion, and ELISA. These tests, each of which utilizes a molecular extract of MAP, have inherently low specificity or sensitivity for MAP and suffer from the disadvantages present with these methods as indicated above.

A significant need exists for a diagnostic method that can be performed rapidly, is highly sensitive, is highly specific, and preferably can be performed by an individual lacking sophisticated laboratory training. Particularly, a significant need exists for such a diagnostic method that is useful for diagnosing diseases such as those caused by MAP.

BRIEF DESCRIPTION OF THE DRAWINGS

FIG. 1 shows that high levels of antibody binding were detected by fluorescent intensity on flow cytometry when serum from cows infected with MAP were mixed with MAP organisms. Flow cytometry following mixing of samples with closely related mycobacterial species resulted in minimal antibody binding and a negative test result for MAP infection.

FIG. 3 shows that serum from cows from farms determined to be MAP free (controls) binds only minimally to MAP organisms, serum from cows determined to be MAP positive show high levels of antibody binding, and that serum from cows from farms having MAP infection but which cows were determined by ELISA to be negative show levels of antibody binding higher than that of controls.

FIG. 5 also contains an insert showing images of stained MAP organisms on dot blot. A: sera from cows from MAP negative farm. B: sera from cows found to be MAP positive by IDEXX ELISA (IDEXX Laboratories, Inc., Westbrook, Me., USA).

DESCRIPTION OF THE INVENTION

Figure 1:
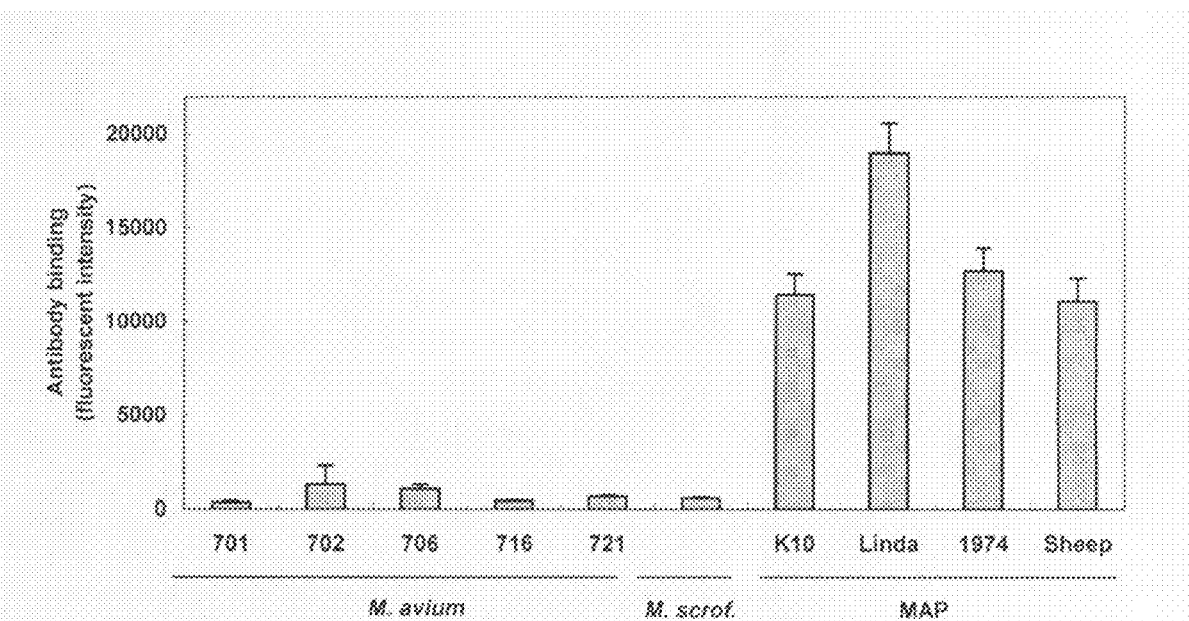
FIG. 1 is a bar graph showing the high specificity of the method of the invention. Each bar represents the mean fluorescence intensity (mean +/−standard deviation of triplicate data) as determined by flow cytometry.

In one embodiment, the invention is a method for diagnosing an infection in an animal caused by a microorganism. The diagnostic method of the invention is based on antibody binding to one or more specific antibody binding sites that exist or existed on the surface of a particular microorganism. In accordance with this method, a test sample, preferably a serum sample, is obtained from an animal suspected of being infected with a microorganism. The test sample thus obtained is exposed to a population of the microorganism. It is then determined if the test sample contains an antibody that binds to the microorganism, preferably to the surface of the microorganism. The test is positive for infection with the microorganism if antibodies in the test sample bind to the microorganism.

The method of the invention is distinct from presently utilized methods for microbial diagnosis and provides several advantages that are unobtainable from such methods. Unlike culture methods, the method of the invention does not require isolation of an organism from an infected animal or the need to culture an organism in vitro. Therefore, the method of the invention provides results in a much shorter time period than is achievable with culture methods and, in contrast to culture methods, can provide a positive diagnosis even during times when the microorganism is not able to be isolated from a host animal.

Unlike recent innovations in microbial diagnosis such as those based on nucleic acid or protein identification, the method of the invention is not based on the determination of the presence of any specific macromolecule peculiar to a particular organism. Also, unlike tests based on antibody binding, such as ELISA testing, the method of the invention does not present an antibody to determine if it binds to an extract of a microorganism or portion of a microorganism that is present in a host animal. Rather, the method of the invention is based upon determining that one or more antibodies present in a test sample isolated from the body of a host animal binds to a particular microorganism that is brought into contact with the test sample.

Thus, the method of the invention provides several advantages previously unobtainable by present diagnostic methods. The method of the invention may be performed rapidly. In a field version of the method of the invention, a positive or negative test result may be obtained rapidly, typically within about two hours. The method of the invention is extremely sensitive, more sensitive than presently available methods. The method of the invention can be used to provide a positive diagnosis even during periods when a microbial pathogen is not detectable in, or isolatable from, a host animal. Additionally, the method of the invention has a specificity that is higher than is obtained with other presently available methods of diagnosis.

The method of the invention is useful for the diagnosis of microbial infections in animals. Such animals include mammals, such as humans and non-human primates, carnivores such as dogs, cats, bears, and weasels, ungulate ruminants and non-ruminants such as horses, cattle, goats, sheep, pigs, non-ungulate ruminants such as camels and llamas, pinnipedia such as seals and sea lions, lagomorpha such as rabbits and hares, rodentia such as squirrels, rats, and mice, cetacea such as whales, dolphins, and porpoises, and proboscidea such as elephants. Such animals also include non-mammalian vertebrates such as birds, reptiles, amphibians, and fish.

A suitable test sample that is obtained from an animal in accordance with the method of the invention may be any fluid or tissue in which an antibody that specifically binds to a suspected causative organism would be present if the animal were infected with that organism. Typically, the test sample is blood or a portion thereof, such as plasma or preferably serum. However, it is contemplated that other sample sources may be utilized in accordance with the invention. The selection of such source of test sample will vary depending, primarily, on the symptoms and signs of an infected animal and the suspected cause of such symptoms or signs. Thus, the test sample may be obtained from fluids such as saliva, milk, pus, tears and other ocular discharges, nasal discharges, sputum, cerebrospinal fluid, peritoneal or pleural fluid, urine, feces, and vaginal, uterine, or urethral secretions and discharges. Fluids may also include those that are produced as part of a pathologic process such as exudates or transudates, such as from the skin, the pleural or peritoneal cavity, the oral cavity, or from the digestive, respiratory, or genital system. The test sample may also be a solid tissue sample if appropriate for diagnosis of a particular disease.

The test sample may be obtained by whatever method is appropriate to obtain such a sample. Thus, the test sample may be obtained by methods such as syringe withdrawal of fluid, including vascular puncture, such as by venipuncture, or by withdrawal of fluid from other sources as described above, or by biopsy.

The organism that is diagnosed by the method of the invention is any microorganism that is capable of eliciting an antibody response in an animal infected by such microorganism. Thus, infective microorganisms that may be diagnosed by the method of the invention include bacteria, fungi, viruses, protozoa, rickettsia, and chlamydia.

The invention is described in detail herein with reference to mycobacterial infections, and particularly with reference to *Mycobacterium avium*, and most particularly with reference to *Mycobacterium avium* subsp. *paratuberculosis* (MAP), the causative organism of Johne's Disease in cattle and Crohn's Disease in humans. This organism has proven to be a very difficult organism to establish as the cause of disease symptoms in cattle and in people and presents, therefore, a significant test to establish the efficacy, specificity, and sensitivity of the method of the present invention.

The test sample may be exposed to a population of microorganism in any way that permits antibodies that are contained in the test sample to interact with the microorganisms. Thus, in a preferred embodiment, the test sample and the microorganism are combined in a vessel such as a test tube or a well and are mixed together, such as by stirring or tapping the exterior of the test tube or well. The test sample and the microorganism may also be reacted together on a surface such as on a slide, filter, or membrane, such as a nitrocellulose membrane.

In a preferred embodiment of the invention, the test sample is exposed to a population of intact whole microorganisms. In this way, antibody binding sites on the entire surface of the microorganism are available for binding to antibodies in the test sample. It is preferred, if intact microorganisms are used, that the microorganisms be killed so as to avoid the risk of infection to humans and to other animals.

A preferred method for killing the microorganisms is by exposure of the microorganisms to a chemical fixative. One preferred chemical fixative is formaldehyde which, when used to kill MAP organisms, maintains the ability of surface antibody binding sites of MAP to bind with antibodies in serum from animals infected with the organism. A preferred concentration of formaldehyde is about 1% to 10% v/v, with a concentration of about 2% most preferred. Other chemical fixatives that may be used to kill microorganisms for use in the method of the invention include non-coagulant fixatives such as acetone, glyceraldehydes, glutaraldehyde, and paraformaldehyde, and less preferred coagulant fixatives such as ethanol and mercuric chloride. Ethanol, in concentrations tested by the inventors (70% v/v), destroyed the ability of surface antibody binding sites of MAP to bind with antibodies in serum from MAP infected animals. It is conceived that coagulant fixatives such as ethanol may be useful for killing microorganisms to be used in the method of the invention, especially if used to diagnose infections by microorganisms other than MAP, or that certain concentrations of such fixatives may be suitable for killing microorganisms and may not render the killed microorganisms unsuitable for the method of the invention. Because of this uncertainty concerning ethanol, coagulant fixatives such as ethanol are less preferred.

The method of the invention may alternatively be performed by exposing the test sample to a population of disrupted or partial microorganisms, such as microorganisms that have been fractionated, or to one or more isolated antibody binding sites of the surface of a microorganism. Such portions of microorganisms preferably contain a significant portion of the surface of the microorganism so as to present a variety of surface antibody binding sites to the antibodies in a test sample. Thus, according to the method of the invention, exposing a test sample to a population of microorganism includes exposing the test sample to intact microorganisms, to disrupted or partial organisms, or to one or more isolated antibody binding sites of a microorganism.

Following the exposure of the test sample to the population of microorganisms, it is then determined if the combination contains conjugates of antibodies from the test sample and microorganisms from the population. Any method that is suitable to detect the presence of antibody binding to an antigen is suitable for the method of the invention.

In one preferred embodiment, antibody-microorganism binding is determined by flow cytometry. Such flow cytometry determination may be performed by analysis of a sample obtained by mixing a suspension containing a serum sample and a population of microorganisms with a labeled anti-antibody, typically a fluorescein-labeled anti-antibody. In another preferred embodiment, antibody-microorganism binding is determined by blot analysis, such as dot blot or Western blot analysis. Such dot blot determination may be performed by mixing a suspension containing a serum sample and a population of microorganisms with an anti-antibody which is labeled, such as with biotin or colloidal gold, spotting this mixture on a membrane, such as a nitrocellulose or polyvinylidene fluoride (PVDF) membrane, and determining the presence of labeled microorganism fixed on the membrane. As detailed below, diagnosis of infection with such methods is accurate, sensitive, and specific. Determination of infection with methods such as dot blot analysis permits diagnosis to be made by visual inspection and such methods are therefore capable of being performed by individuals who are not technically trained in sophisticated laboratory techniques.

The invention is further illustrated in the following non-limiting examples.

EXAMPLE 1

Technique for Serological Diagnostic Test Using Flow Cytometry

Two microliters of serum samples obtained from bovine subjects and 49 microliters of phosphate-buffered saline-10% Superblock (Pierce Biotechnology, Inc., Rockford, Ill. USA)-0.05% Tween (buffer A) were added to a population of whole organisms of *Mycobacterium* species (5 microliters packed volume) to form a suspension of organisms. The suspension was incubated at room temperature for 1 hr, washed three times with 100 microliters buffer A by centrifugation at 5000 rpm for 10 min, mixed with fluorescent-labeled rabbit anti-bovine IgG antibody (MP Biomedicals (formerly ICN Biomedicals), Irvine, Calif., USA) diluted 1:50 in buffer A, incubated at room temperature for 1 hr, and washed twice with buffer A by centrifugation at 5000 rpm for 10 min. One tenth of the volume of the treated organisms was resuspended in 1 ml of buffer A and fluorescence on 10,000 organisms was analyzed by using a flow cytometer (LSR II, BD Biosciences, San Jose, Calif., USA).

EXAMPLE 2

Alternative Technique for Serological Diagnostic Test by Flow Cytometry

The method of the invention was performed utilizing a simplified alternative technique for serological diagnosis by flow cytometry. This alternative technique requires a shorter time than the technique described in Example 1 and does not require centrifugation.

One microliter of bovine serum, 5 microliters of fluorescent-labeled rabbit anti-bovine IgG antibody (1.5 mg/ml), and 44 microliters of buffer A were added to whole organisms of MAP (5 microliters packed volume), and incubated at room temperature for 1 hr. One tenth of the treated organisms were suspended in 1 ml buffer A and fluorescence on 10,000 organisms was analyzed using a flow cytometer.

EXAMPLE 3

Serological Diagnostic Test Using a Dot Blot Technique

One microliter of bovine serum samples and 9 microliters of buffer A were added to whole organisms of MAP (5 microliters packed volume), and incubated at room temperature for 1 hr. The organisms were washed three times with 100 microliters of buffer A by centrifugation at 5000 rpm for 10 min, mixed with undiluted colloidal gold-labeled rabbit anti-bovine IgG antibody (Jackson ImmunoResearch Laboratories, Inc., West Grove, Pa., USA), incubated at room temperature for 1 hr, and washed twice with 100 microliters of buffer A by centrifugation at 5000 rpm for 10 minutes. The treated organisms were resuspended in 100 microliters of buffer A and spotted on a PVDF membrane (Bio-Rad Laboratories, Inc., Hercules, Calif., USA) by using a dot blot apparatus (Bio- Rad). Images of the stained organisms on the dot blot were captured, and their densitometric intensities measured, using a gel documentation system (ChemiDoc XRS, Bio-Rad).

EXAMPLE 4

Specificity of the Method of Invention

Pooled and individual serum samples from cows known to be infected with MAP were analyzed as described in Example 1. Serum samples from cows known to be infected with MAP were mixed with organism populations that were one of 5 strains of *Mycobacterium avium* subsp. *avium* (MAA), one strain of *Mycobacterium scrofulaceum*, or 4 strains of MAP, respectively prior to detection of binding by flow cytometry. Results are shown in FIG. 1.

As shown in FIG. 1, the method of the invention correctly identified infection with MAP in all samples and showed a lack of false positive diagnoses as the method of the invention did not show binding when bacterial populations closely related to MAP were used as the test organism. This study establishes the high specificity of the method of the invention, which is capable of distinguishing between very closely related organisms.

EXAMPLE 5

Specificity of the Method of the Invention

Serum samples from 8 cows known to be infected with MAP were pooled. The pooled serum sample was tested as described in Example 1 by combining individual 2 microliter samples of the pooled serum sample with one of 8 different strains of MAP or with MAA. Results are shown graphically in FIG. 2.

Figure 2:
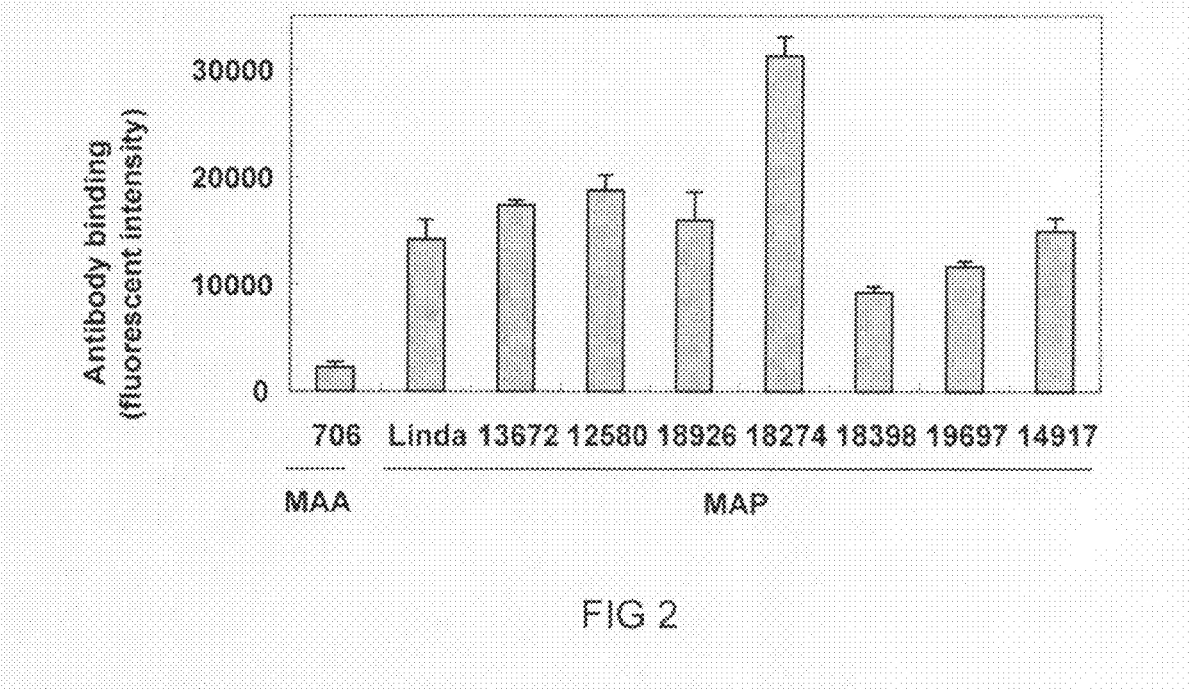
FIG. 2 is a bar graph showing the high specificity of the method of the invention. Each bar represents the mean fluorescence intensity (mean +/−standard deviation of triplicate data).

As shown in FIG. 2, minimal antibody binding as shown by fluorescent intensity was found for the sample that was mixed with MAA organisms. In contrast, a very high level of antibody binding was determined for each of the serum samples combined with MAP organisms. This study establishes the high specificity of the method of the invention, which is capable of distinguishing between very closely related organisms, even between MAP and MAA, and specifically identified infection with MAP even when different strains of MAP were used as the test microorganism.

EXAMPLE 6

Sensitivity of the Method of the Invention

The method of the invention utilizing whole MAP organisms, as described in Example 1, was tested in comparison with an ELISA-based test HerdChek® *Mycobacterium paratuberculosis* Test Kits (Johne's Disease) (IDEXX Laboratories, Inc., Westbrook, Me., USA). The method of the invention was performed according to the procedure of Example 1 utilizing (1) sera from cows in farms that were determined to be free of MAP infection (MAP Free, n=8), (2) sera from cows in farms with MAP infection, which cows were determined by the IDEXX HerdChek® ELISA test to be MAP negative (MAP Negative, n=5), and (3) sera from cows that were determined by the IDEXX HerdChek® ELISA to be MAP positive (MAP Positive, n=14). Resultant data are shown in Table 1.

In Table 1, the mean (2429)+2 S.D. of MAP Free serum results (4164) was used as a cut-off value to evaluate MAP infections of tested MAP Negative and MAP Positive cows. All (100%) of samples diagnosed as positive by the IDEXX ELISA test were diagnosed as positive by the method of the invention. Additionally, two of five (40%) of the samples determined by the IDEXX ELISA test to be negative were diagnosed as positive by the method of the invention.

TABLE 1

| Serum Samples | Fluorescent intensity of antibody binding |
|---|---|
| MAP Free | 2085 2215 1250 4140 1701 2471 2794 2777 |
| MAP Negative | <u>4914</u> 2411 <u>6900</u> 4120 3779 |
| MAP Positive | 16012 8487 7129 7468 20455 7719 13734 12344 25893 15970 13392 8549 10497 17799 |

MAP Free (n = 8) - all samples found to be negative by ELISA testing were determined to be negative by the method of the invention.
MAP Negative (n = 5) - 2 of 5 samples (40%) positive by method of invention. Results of samples found negative by ELISA testing but positive by the method of the invention are <u>underlined</u>.
MAP Positive (n = 14) - all samples found to be positive by ELISA testing were determined to be positive by the method of the invention.

Figure 3:
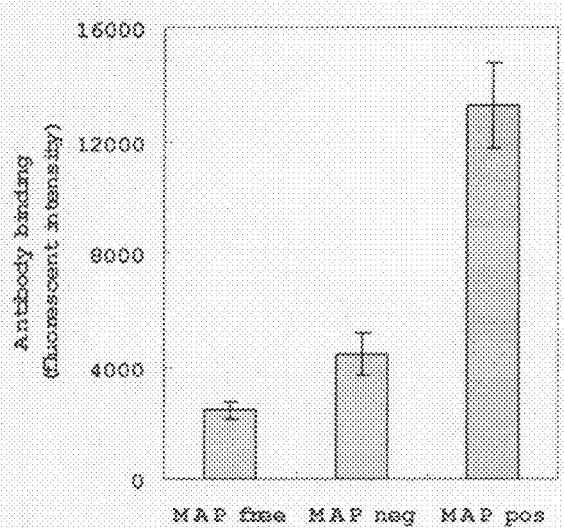
FIG. 3 is a bar graph showing the high sensitivity of the method of the invention. Each bar represents the mean fluorescence intensity (mean +/−standard error of triplicate data) as determined by flow cytometry.

The data from this study is summarized in the bar graph of FIG. 3. In FIG. 3, the average antibody binding, as determined by fluorescent intensity, is shown for each of three types of samples, cows from MAP free farms, cows from MAP positive farms but which have been determined by IDEXX ELISA test to be MAP negative, and cows determined to be positive for MAP by IDEXX ELISA test.

The data of Table 1 and FIG. 3 establish that the method of the invention is more sensitive than that of the most commonly used non-culture method presently in use for diagnosing Johne's Disease in cattle. The IDEXX ELISA test had a false negative rate of 40% as established when later confirmed with the method of the invention, in which the false negative rate was 0%.

EXAMPLE 7

Alternative Technique for Diagnosis of MAP by Flow Cytometry

Sera from cows determined by IDEXX ELISA to be MAP negative were pooled and sera from cows determined by IDEXX ELISA to be MAP positive by IDEXX ELISA test were pooled to provide two samples. The samples were tested for the presence of MAP infection by the simplified, alternative technique described in Example 2. MAP organisms, pooled serum, and fluorescent-labeled secondary antibody were mixed, incubated for 1 hr, and antibody binding to MAP was determined by flow cytometry. The results were compared with a control sample which contained MAP organisms and secondary antibody but no serum. Results are shown in the bar graph of FIG. 4.

Figure 4:
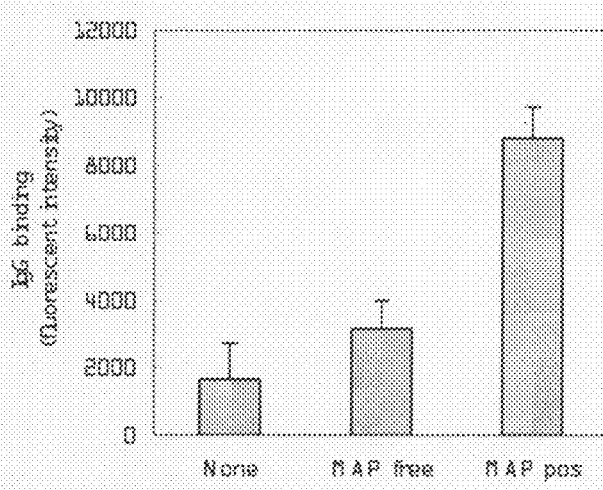
FIG. 4 is a bar graph showing the high sensitivity of the method of the invention utilizing the simplified procedure of Examples 2 and 7. Each bar represents the mean densimetric intensity (mean +/−standard deviation of triplicate data) as determined by flow cytometry.

As shown in FIG. 4, the control sample (None) showed a low level of fluorescent activity as determined by flow cytometry. Additionally, the MAP positive serum showed a very high level of fluorescent activity indicating a high level of serum antibody binding with the MAP organisms. Unexpectedly, the fluorescent activity of the MAP free pooled sera, that found to be negative by ELISA test, showed a level of fluorescent activity about twice that of control. This result indicates that the ELISA test incorrectly identified MAP infected cows as being free of infection. The diagnostic test according to the invention, however, correctly identified that antibodies due to MAP infection were present in the pooled serum from this group.

The results of this study establish that, even with a simplified procedure requiring a shortened processing time and no centrifugation, the method of the invention is more sensitive than the most commonly used present method for diagnosis of MAP infection in cattle. Additionally, because portable flow cytometers are commercially available, the method of the invention is useful for field, onsite diagnosis.

EXAMPLE 8

Diagnosis of MAP by Dot Blot Technique

Sera from cows found to be MAP negative by ELISA test were pooled and sera from cows found to be MAP positive by ELISA test were pooled to provide two samples. The samples were treated as described above in Example 3 and diagnosed by dot blot technique. The results are shown in FIG. 5.

Figure 5:
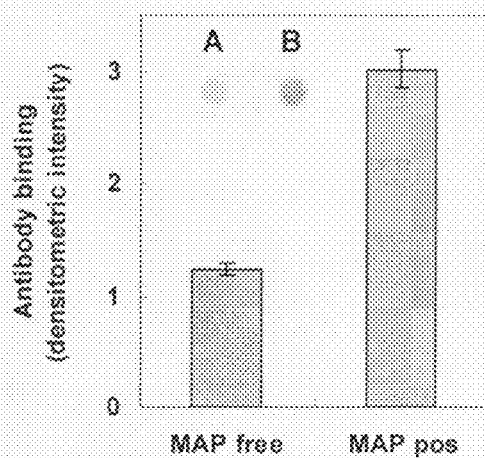
FIG. 5 is a bar graph showing results of the method of the invention for diagnosing MAP infection using a dot blot procedure. Each bar represents the mean fluorescence intensity.

As shown in FIG. 5, the dot blot technique of the invention showed a high degree of antibody binding in sera from cows previously found to be MAP positive by ELISA test. Additionally, antibody binding to MAP was detected by this method even in sera from cows previously found to be negative by ELISA testing, establishing the high sensitivity of the method of the invention as performed by dot blot technique.

The dot blot technique is a simple method that can be performed easily in the laboratory by trained personnel. Additionally, because results of dot blot technique are evaluated visually, this technique can be performed in field conditions even by individuals not trained in laboratory techniques. Thus, the method of the invention is useful for both laboratory and field diagnosis of MAP infected individuals, and such diagnosis may be performed by either technical or non-technical personnel.

Further modifications, uses, and applications of the invention described herein will be apparent to those skilled in the art. It is intended that such modifications be encompassed in the claims that follow.

The invention claimed is:

1. A method for diagnosing the presence in an animal of an infection caused by a microorganism comprising obtaining a test sample from the animal, exposing the test sample to a population of the microorganism for a time sufficient to permit an antibody in the test sample that binds to an antibody binding site of the microorganism to bind to the antibody binding site, then putting the microorganisms that were exposed to the test sample in suspension, exposing the test sample and the population of the microorganisms to a labeled anti-antibody before, during, or after the microorganisms that were exposed to the test sample are put in suspension, determining a quantitative level of binding of the suspended microorganisms to antibodies in the test sample by detecting an absolute level of the label that is bound to the microorganisms, and comparing the level of the antibody binding in the test sample with the level of antibody binding from a negative control, wherein the presence of infection is diagnosed if the level of antibody binding in the test sample is higher than that in the control.

2. The method of claim 1 wherein the animal is a mammal.

3. The method of claim 2 wherein the mammal is a bovine.

4. The method of claim 1 wherein the microorganism is a bacterium.

5. The method of claim 4 wherein the bacterium is a mycobacterium.

6. The method of claim 5 wherein the mycobacterium is *Mycobacterium avium* subsp. *parcatuberculosis*.

7. The method of claim 1 wherein the test sample is serum.

8. The method of claim 7 wherein the serum test sample is obtained from the animal by venipuncture.

9. The method of claim 1 wherein the test sample is a fluid or bodily discharge selected from the group consisting of saliva, milk, pus, ocular discharge, nasal discharge, sputum, cerebrospinal fluid, peritoneal fluid, pleural fluid, urine, feces, vaginal secretion or discharge, uterine secretion or discharge, urethral secretion or discharge, extidate, and transudate.

10. The method of claim 1 wherein the population of the microorganism contains intact whole microorganisms.

11. The method of claim 10 wherein the intact whole microorganisms are killed microorganisms.

12. The method of claim 1 wherein the detection of the level of binding is by blot analysis.

13. A method for diagnosing infection caused by *Mycobacterium avium* subsp. *paratuberculosis* (MAP) in an animal comprising obtaining a test sample front the animal, exposing the test sample to a population of MAP organisms for a time sufficient to permit an antibody in the test sample that binds to an antibody binding site of MAP to bind to the antibody binding site, then putting the MAP microorganisms that were exposed to the test sample in suspension, exposing the test sample and the population of the MAP microorganisms to a labeled anti-antibody before, during, or after the MAP microorganisms that were exposed to the test sample are put in suspension, determining a quantitative level of binding of the MAP organisms to antibodies in the test sample by detecting an absolute level of the label that is bound to the microorganisms, and comparing the level of the antibody binding in the test sample with the level of antibody binding from a negative control, wherein the presence of MAP infection is diagnosed if the level of antibody binding in the test sample is higher than that in the control.

14. The method of claim 13 wherein the infection is Johne's Disease.

15. The method of claim 13 wherein the animal is a bovine.

16. The method of claim 13 wherein the test sample is serum.

17. The method of claim 13 wherein intact whole MAP organisms are exposed to the test sample.

18. The method of claim 17 wherein the intact whale MAP organisms are killed.

19. The method of claim 13 wherein the detection of the level of binding is by blot analysis.

* * * * *